United States Patent [19]

Berg et al.

[11] 4,273,571

[45] Jun. 16, 1981

[54] ORGANIC CHEMICAL COMPOUND, MICROBIOLOGICAL PROCESS FOR ITS PREPARATION, AND ITS USE AS A HERBICIDE

[75] Inventors: Dieter Berg; Werner Frommer; Delf Schmidt, all of Wuppertal; Robert R. Schmidt, Cologne; Dietmar Schäfer, Marburg, all of Fed. Rep. of Germany

[73] Assignee: Bayer Aktiengesellschaft, Leverkusen, Fed. Rep. of Germany

[21] Appl. No.: 967,930

[22] Filed: Dec. 8, 1978

[30] Foreign Application Priority Data

Dec. 24, 1977 [DE] Fed. Rep. of Germany ....... 2758008
Feb. 11, 1978 [DE] Fed. Rep. of Germany ....... 2805855

[51] Int. Cl.$^3$ ..................... A01N 63/04; C12P 13/00; C12P 1/06
[52] U.S. Cl. ........................................... 71/79; 71/65; 435/128; 435/169; 435/822; 435/827; 424/118
[58] Field of Search ................... 71/79; 435/128, 169, 435/822, 827; 260/236.5

[56] References Cited

U.S. PATENT DOCUMENTS 3,501,456  3/1970  Shen et al. .............................. 536/23

OTHER PUBLICATIONS

Stout et al., "J. of Het. Chem.," (1971) 8 (3), pp. 515–516.

*Primary Examiner*—Glennon H. Hollrah
*Attorney, Agent, or Firm*—Sprung, Felfe, Horn, Lynch & Kramer

[57] ABSTRACT

A herbicidally active compound of the empirical formula $C_{10}H_{14}N_6O_3$, exhibiting substantially the IR KBr-absorption spectrum shown in FIG. 2, is produced by aerobic culturing of a micro-organism of the family of the Actinoplanaceae under aerobic conditions in a nutrient medium which contains an assimilable carbon source, at least one assimilable nitrogen source and mineral salts, at a pH of 6 to 8 and a temperature of 20° to 40° C.

6 Claims, 4 Drawing Figures

ORGANIC CHEMICAL COMPOUND, MICROBIOLOGICAL PROCESS FOR ITS PREPARATION, AND ITS USE AS A HERBICIDE

The present invention relates to a new herbicidally active compound produced microbiologically.

It has already been disclosed that a species of Streptomyces (S. Saganonens) forms two herbicidally active components, namely Herbicidine A and Herbicidine B [Journal of Antibiotics 29 (9), 863–869 (1976); ibid 29 (9), 870–875 (1976)].

The present invention microbiologically produces a different compound characterized by empirical formula $C_{10}H_{14}N_6O_3$ and by the IR KBr-absorption spectrum reproduced in FIG. 2 (abscissa: wave number in $cm^{-1}$, ordinate: extinction), which exhibits characteristic bands at wave numbers 3340, 3170, 2920, 2040, 1660, 1600, 1570, 1520, 1480, 1430, 1380, 1340, 1295, 1250, 1215, 1160, 1110, 1030, 890, 860, 790 and 720 $cm^{-1}$.

The compound can furthermore be described in terms of the following properties and parameters:

(1) Elementary analysis (after drying for 4 days in a high vacuum at 100° C.)

Calculated: C 45.11, H 5.30, N 31.57, O+ 18.03;
Found: C 45.0, H 5.5, N 31.2, O+ 18.03; +calculated by difference.

(2) Decomposition point

The substance forms a white amorphous powder having a decomposition point of 134°–135° C.

(3) Specific optical rotation $[\alpha]_D^{20} = -10.7°$ (C=1.0% in methanol).

(4) Molecular weight determination

The molecular weight was determined titrimetrically to be 258. In the field desorption mass spectrum a quasimolecule ion corresponding to a molecular weight of 266 was observed.

(5) Ultraviolet absorption spectrum

The UV spectrum of the compound is reproduced in FIG. 1 (abscissa: wavelength in nm, ordinate: extinction).

The compound has a characteristic spectrum in the ultraviolet region, with $\lambda=259$ in $H_2O$ (FIG. 1, curve b), $\lambda_{max}=259$ in 0.1 N $NaOH_{max}$ (FIG. 1, curve a) and $\lambda_{max}=257$ in 0.1 N HCl (FIG. 1, curve c); in $H_2O$, $E_1\,cm^{1\%}=401$ at 259 nm, in 0.1 N NaOH, $E_1\,cm^{1\%}=341$ at 259 nm and in 0.1 N HCl $E_1\,cm^{1\%}=337$ at 257 nm.

(6) $^1H$ 60 Mc/s nuclear resonance spectrum (reproduced in FIG. 3).

The $^1H$-NMR spectrum of the compound in $D_2O$ exhibits characteristic resonances at $\delta=8.25$, 6.27 (doublet) and 3.50 ppm (doublet, broad).

(7) Mass spectrum (reproduced in FIG. 4)

In the mass spectrum, characteristic fragment ions are found at 236, 213, 177, 164, 136, 135, 131 and 108.

(8) The compound is readily soluble in water, aqueous methanol and aqueous ethanol, sparingly soluble in anhydrous methanol and anhydrous ethanol and insoluble in ethyl acetate, butyl acetate and benzene.

(9) The compound according to the invention can be hydrolyzed in acid media. Thus, for example, two cleavage products are found on 20 minutes' treatment with 6 N hydrochloric acid. One cleavage product exhibits the characteristic UV spectrum, while the other is a carbohydrate constituent of the starting material.

(10) The compound according to the invention is an amorphous colorless basic material. Since a carbohydrate constituent is split off on acid hydrolysis, it is readily possible to stain the intact compound, in thin layer chromatography on a silica gel plate, by means of sugar reagents (for example anisaldehyde/sulphuric acid or thymol/sulphuric acid). Some reactions used for identifications are listed in Table 1. (11) The $R_f$ values of the compound according to the invention, on neutral silical gel plates, are shown in Table 2.

(12) The antibiotic action of the compound according to the invention is low. Thus with 100 μg no inhibition of E. coli can be observed. At 3 μg, the inhibition of Staph. aureus is slight.

TABLE 1

Experiments on the chemical coloration reactions of the compound

| No. | Reagent/name of reaction+ | Coloration |
|---|---|---|
| 1 | ninhydrin | + |
| 2 | Morgan/Elson | + |
| 3 | 4-dimethylaminobenzaldehyde | + |
| 4 | alkaline $KMnO_4$ | + |
| 5 | thymol/$H_2SO_4$ | + |
| 6 | anisaldehyde/$H_2SO_4$ | + |
| 7 | periodate | + |
| 8 | 2',7'-dichlorofluorescein | + |
| 9 | iodine | + |
| 10 | Bromocresol Green | − |
| 11 | rhodamine B | − |
| 12 | phosphomolybdic acid | − |
| 13 | aniline phthalate | − |
| 14 | Tollen's reagent | − |
| 15 | diphenylamine | − |
| 16 | 2,4-dinitrophenylhydrazine | − |
| 17 | iron(III) chloride | − |

+The reagents were made up in accordance with the usual instructions (see E. Stahl, Dünnschichtchromatographie (Thin Layer Chromatography), 2nd edition, Springer-Verlag Berlin-Heidelberg-New York, 1967).

TABLE 2

Characterization of the compound by thin layer chromatography on Kieselgel 60, F 254, layer thickness 0.25 mm (Merck)

| Eluant system (parts by volume) | $R_f$ values |
|---|---|
| n-butanol/glacial acetic acid/$H_2O$ = 50/25/25 | 0.27 |
| chloroform/methanol/glacial acetic acid = 90/8/2 | 0.05 |
| chloroform/methanol/$H_2O$ = 80/20/2.5 | 0.09 |
| acetone | 0.04 |
| chloroform/methanol = 80/20 | 0.12 |
| chloroform/methanol = 90/10 | 0.03 |
| chloroform | 0 |
| diethyl ether | 0 |
| chloroform/methanol/ammonia = 20/3/0.5 | 0.04 |
| n-butyl acetate/n-butanol/glacial acetic acid/phosphate buffer of pH 7 = 50/10/25/15 | 0.08 |
| i-propanol/2 N ammonia/$H_2O$ = 7/1/2 | 0.40 |

Further, it has been found that the compound according to the invention is obtained if micro-organisms of the family of the Actinoplanaceae are cultured under aerobic conditions in a nutrient medium which contains assimilable sources of carbon and nitrogen as well as mineral salts, and the compound is isolated.

Suitable micro-organisms for carrying out the process according to the invention are those of the genera Amorphosporangium, Spirillospora, Dactylosporangium, Planomospora, Planobispora, Kitasatoa, Microellobosporia, Elytrosporangium, Microechinospora and Intrasporangium. The use of micro-organisms of the genera Actinoplanes, Ampullariella and Pilimelia is preferred. The use of strains of the genus Streptosporangium is very particularly preferred.

With regard to the genus Streptosporangium, it is surprising that it forms the compound according to the invention, since, according to statements in the literature [see, for example, J. Berdy in Advances in Applied Microbiology, Vol. 18, 1974, page 309, Academic Press, New York] the genus Streptosporangium does not give nearly as good a yield, in respect of the formation of secondary compound, as, for example, the closely related genus Streptomyces.

In particular, the Streptosporangium strains SS 237 (CBS 545.77), SS 243 (CBS 544.77), SS 248 (CBS 543.77) and SS 268 (CBS 542.77) can be used to carry out the process according to the invention.

These strains belong to the class of the Schizomycetes, the order Actinomycetales, the family of Actinoplanaceae and the genus Streptosporangium. All strains were isolated from soil. The strains have the following characteristics:

TABLE 3

| Strain number | SS 237 | SS 243 | SS 248 | SS 268 |
|---|---|---|---|---|
| Genus | Streptosporangium | Streptosporangium | Streptosporangium | Streptosporangium |
| Origin | Austria, Mittersill im Pinzgau; humus soil | Sweden, Anesåt; soil from the edge of a water course | Persia, Elburs mountains; soil from the top of the pass on the Teheran-Amul road | Denmark, near the German frontier; humus soil |
| Date of isolation | 6.2.1974 | 8.2.1974 | 14.2.1974 | 21.2.1974 |
| Enrichment procedure | soil sample smear on agar plate | soil sample smear on agar plate | soil sample smear on agar plate | soil sample smear on agar plate |
| Substrate mycelium | about $0.3-1\mu$ wide | about $0.3-0.9\mu$ wide | about $0.3-0.9\mu$ wide | about $0.3-0.9\mu$ wide |
| Aerial mycelium | mostly about $0.8-1\mu$ wide, branched, septate; white, dirty white, pale pink if there is good formation of sporangia | mostly about $0.8-1\mu$ wide, branched, septate; white | mostly about $0.8-1\mu$ wide, branched, septate; white, pink if there is good formation of sporangia | mostly about $0.8-1\mu$ wide, branched, septate; white |
| Shape of sporangia | spherical | spherical | spherical | spherical |
| Size of sporangia (on KEHE agar) | $3-15\mu$, mostly $7-13\mu$ | $3.13\mu$, mostly $6-11\mu$ | $3-16\mu$, mostly $8-13\mu$ | $3-13\mu$, mostly $6-10\mu$ |
| Shape of spores | ellipsoid | ellipsoid, in part also spherical | ellipsoid | ellipsoid, in part also spherical |
| | non-flagellate | non-flagellate | non-flagellate | non-flagellate |
| Spore size | mostly $1 \times 1.3-1.5\mu$ | about $0.8-1 \times 1-1.5\mu$ | about $0.9-1.3 \times 1-1.8\mu$, occasionally also longer | mostly $1 \times 1.3-1.4\mu$, when spherical $1-1.4\mu\ \phi$ |

TABLE 4

| Strain number | SS 237 | | SS 243 | | SS 248 | | SS 268 | |
|---|---|---|---|---|---|---|---|---|
| Melanin formation on | CPC-agar | − | CPC-agar | − | CPC-agar | − | CPC-agar | − |
| | Ty-agar | − | Ty-agar | − | Ty-agar | − | Ty-agar | − |
| | gelatine | − | gelatine | − | gelatine | − | gelatine | − |
| Nitrate reduction | − | | + | | − | | − | |
| Gelatine liquefaction | − | | − | | − | | − | |
| Milk peptonization | + (slight) | | + (slight) | | + | | + | |
| Tyrosine dissolution | − | | + | | − | | − | |
| Growth at 15° C. | + | | + | | + | | + | |
| 20° C. | + | | + | | + | | + | |
| 27° C. | + | | ++ | | + | | ++ | |
| 32° C. | + | | + | | ++ | | + | |
| 37° C. | + | | + | | + | | + | |
| 42° C. | − | | − | | − | | − | |
| Starch hydrolysis | ++ | | + | | ++ | | + | |
| L-Arabinose | ++ (!) | | ++ | | ++ (!) | | ++ (!) | |
| D-Fructose | ++ (!) | | ++ (!) | | ++ (!) | | ++ (!) | |
| D-Glucose | ++ (!) | | ++ | | ++ | | ++ (!) | |
| i-Inositol | − | | − | | ++ | | − | |
| Lactose | − | | − | | + | | + | |
| D-Mannitol | ++ (!) | | ++ (!) | | ++ (!) | | ++ (!) | |
| Raffinose | − | | − | | + | | − | |
| L-Rhamnose | ++ (!) | | + | | ++ (!) | | ++ (!) | |
| Sucrose | ++ (!) | | ++ (!) | | ++ (!) | | ++ (!) | |
| D-Xylose | ++ (!) | | − | | ++ (!) | | ++ (!) | |

TABLE 5

| Strain number | SS 237 | SS 243 | SS 248 | SS 268 |
|---|---|---|---|---|
| Flaked oats/ yeast agar (HaH) | G good<br><br>SM brownish orange and brown<br><br>AM +, predominantly as a thin hoarfrost-like covering; white and dirty yellowish<br><br>SP brown in the immediate vicinity of the mycelium<br><br>GC about 10 mm φ; surface ridged and humped; edge lobed, sharply separated from the nutrient medium; SM orange at the edge of the colony, orange-brown and brown towards the center | G good<br><br>SM strong orange-red<br><br>AM −<br><br><br><br><br>SP −<br><br><br><br>GC about 10 mm φ; surface, apart from a narrow flat edge zone, humped and furrowed, edge lobed, sharply separated from the nutrient medium; SM deep orange-red | G good<br><br>SM orange-red<br><br>AM −<br><br><br><br><br>SP −<br><br><br><br>GC about 8 mm φ; surface humped; narrow, flat transparent edge zone; SM deep orange | G good<br><br>SM light orange-red<br><br>AM + (slight), white<br><br><br><br><br>SP −<br><br><br><br>GC about 15 mm φ, compact; surface with radially extending channels, convex sectors with concentric grooves, middle of colony ridged; edge lobed, sharply separated from the nutrient medium; SM deep orange-red, AM + near the edge |
| Yeast/ starch agar (E) | G good<br><br>SM reddish brown to reddish dark brown<br><br>AM ++ as a thin hoarfrost-like covering; sporangia +<br><br>SP − to pale yellowish brown<br><br>GC about 10 mm φ, very high in growth; surface scaly; edge lobed, sharply separated from the nutrient medium; SM reddish dark brown | G moderate to good<br><br>SM reddish yellow-brown<br><br><br>AM −<br><br><br><br>SP −<br><br>GC about 10 mm φ, with radial channels, sectors concentrically stepped; edge lobed, sharply separated from the nutrient medium; SM brownish yellow with orange tint | G good<br><br>SM light orange-red<br><br><br>AM ++, predominantly as a thin hoarfrost-like covering<br><br>SP −<br><br>GC about 10 mm φ, very high in growth; surface scaly-warty; edge lobed, sharply separated from the nutrient medium; SM orange | G good<br><br>SM yellow-brown<br><br><br>AM −<br><br><br><br>SP −<br><br>GC about 12 mm φ, with radial channels, sectors concentrically stepped and scaly; edge lobed, sharply separated from the nutrient medium; SM brown-yellow with pale orange tint |
| Casamino/ peptone Czapek agar (CPC) | G moderate to good<br><br>SM yellow-orange<br><br><br>AM −<br><br>SP −<br>GC about 7 mm φ, very high in growth; surface scaly-warty; edge lobed, sharply separated from the nutrient medium; SM yellow-orange | G moderate<br><br>SM orange and pale ochre<br><br>AM −<br><br>SP −<br>GC about 5 mm φ; surface humped, incipient scaling; edge lobed, sharply separated from the nutrient medium<br>SM yellow-orange | G moderate to good<br><br>SM orange<br><br><br>AM ++, very thin, hoarfrost-like covering<br>SP −<br>GC about 5 mm φ; as for SS 243; surface slightly frosted due to slight AM formation | G moderate to good<br><br>SM brownish yellow, in part pale orange<br><br>AM −<br><br>SP −<br>GC about 8 mm φ, with radial channels, sectors concentrically grooved and stepped; edge lobed, sharply separated from the nutrient medium; SM brownish yellow with pale orange tint |
| NO₃ agar | G good<br>SM black-brown<br>AM −<br>SP −<br>nitrate reduction − | G good<br>SM pale brown-orange<br>AM −<br>SP −<br>nitrate reduction + | G good<br>SM pale orange-brown<br>AM −<br>SP −<br>nitrate reduction − | G good<br>SM pale brown-orange<br>AM −<br>SP −<br>nitrate reduction − |
| Skimmed milk agar | G moderate to good<br>SM reddish brown | G moderate<br><br>SM orange | G moderate to good<br><br>SM light brownish red | G good<br><br>SM orange-red |

TABLE 5-continued

| Strain number | SS 237 | SS 243 | SS 248 | SS 268 |
|---|---|---|---|---|
| (Ca) | | | | |
| | AM — | AM — | AM — | AM — |
| | milk slightly peptonized | SP — | SP — | SP — |
| | | milk slightly peptonized | milk partially peptonzied | milk partially peptonized |
| Tyrosine agar (Ty) | G moderate | G slight | G good to moderate | G moderate to good |
| | SM brown | SM yellowish brown | SM yellow-brown | SM reddish brown |
| | AM — | AM — | AM — | AM — |
| | SP — | SP — | SP — | SP — |
| | crystal dissolution — | crystal dissolution + | crystal dissolution — | crystal dissolution — |
| Czapek agar (Cz) | G slight to moderate | G slight | G moderate | G slight |
| | SM brown | SM pale brownish yellow | SM yellowish brown | SM pale brown |
| | AM — | AM — | AM — | AM — |
| | SP pale yellowish brown | SP — | SP — | SP — |
| Soil/ glucose/ yeast agar (EGH) | G slight to moderate | G slight to moderate | G slight to moderate | G slight to moderate |
| | SM brown to dark brown | SM brown | SM brown | SM brown |
| | AM ++, white sporangia ++ | AM +, slight sporangia + | AM ++, white sporangia ++ | AM +, slight sporangia + |
| Synthetic soil decoction/ yeast extract agar (KEHE) | G slight | G slight | G slight | G slight |
| | SM pale orange brown and pale brown | SM brown-orange | SM brown-orange | SM pale orange-brown |
| | AM +, hoarfrost-like, white and pale pink | AM +, hoarfrost-like, white | AM +, hoarfrost-like, white | AM +, slight; white |
| | sporangia ++ | sporangia ++ | sporangia ++ | sporangia + |
| | SP — | SP — | SP — | SP — |

Notes on the tables
G = growth
SM = substrate mycelium
AM = aerial mycelium
SP = substrate-discoloring dyestuff
GC = giant colony In tests for utilization of various carbon sources, the symbols mean the following:

++ growth as good as on mineral salt/vitamin agar with glucose, or better

+ growth better than on pure mineral salt/vitamin agar but less than on mineral salt/vitamin agar with glucose — growth as on pure mineral salt/vitamin agar, or less (!) growth good The strains were cultured at room temperature and in diffuse daylight. After four to six weeks' growth, the culture characteristics on the individual nutrient media were recorded. The data for the giant colonies relate to a period of growth of 6 weeks.

CULTURE MEDIA

Soil/glucose/yeast agar (EGH): soil decoction 250 ml; glucose 0.5 g; yeast extract 0.5 g; agar 15 g; tap water 750 ml.

For the composition of the remaining nutrient media, see Schäfer, D.: "Beiträge zur Klassifizierung und Taxonomie der Actinoplanaceen" ("Contributions to the Classification and Taxonomy of the Actinoplanaceae"), Thesis, Marburg 1973 (especially page 42 et seq.).

For the test regarding utilization of various C sources, the mineral salt agar serving as the base medium was enriched with a vitamin solution, since the four strains showed only slight growth on the simple medium.

Vitamin solution: thiamine 100 mg; biotin 0.1 mg; nicotinic acid amide 100 mg; inositol 1 g; water 100 ml.

1 ml of this vitamin solution was added per liter of mineral salt agar.

The enrichment and isolation of the strains were carried out in accordance with the customary methods (see Schäfer, 1973) by means of a soil sample smear on Petri dishes, incubation for four to six weeks and trans-inoculation of individual sporangia.

All four strains are distinquished by spherical sporangia, formed on the aerial mycelium, with non-flagellated sporangiospores. On the grounds of these morphological characteristics they belong unambigiously to the genus Streptosporangium.

As the tables show, the strains are not identical with one another.

The process according to the invention can be carried out with the aid of solid, semi-solid or liquid nutrient media. Liquid aqueous nutrient media are preferred.

The nutrient media are inoculated in accordance with generally customary methods, for example using slant tubes or flask cultures.

The culture is carried out under aerobic conditions and can be effected in accordance with the generally customary methods, such as using shaken cultures, for example in shaking flasks, air-agitated cultures or submerse cultures. Preferably, the culture is carried out by the aerobic submerse process in aerated fermenters, for example in the customary submerse fermentation tanks.

The culture can be carried out continuously or discontinuously. Preferably, the discontinuous procedure is used.

The culture can be carried out in all nutrient media which are known to be used for cultivating microorganisms of the order Actinomycetales. The nutrient medium must contain one or more assimilable carbon sources and nitrogen sources as well as mineral salts, and these products can be present in the form of defined individual constituents, or in the form of complex mixtures as represented, in particular, by biological products of various origins. As sources of carbon, all customary sources may be used. Examples which may be mentioned are starch, molasses, whey powder, dextrin, sugars, such as sucrose, maltose, glucose and lactose, sorbitol and glycerol. Suitable nitrogen sources are all customary organic and inorganic nitrogen sources. Examples which may be mentioned are soy bean flour, cottonseed flour, lentil flour, pea flour, soluble and insoluble vegetable proteins, corn steep liquor, yeast extract, peptones and meat extract, as well as ammonium salts and nitrates, for example $NH_4Cl$, $(NH_4)_2SO_4$, $NaNO_3$ and $KNO_3$. The mineral salts which should be present in the nutrient medium provide, for example, the following ions: $Mg^{++}$, $Na^+$, $K^+$, $Ca^{++}$, $NH_4^+$, $Cl^-$, $SO_4^{--}$, $PO_4^{---}$ and $NO_3^-$, as well as ions of the customary trace elements, such as Cu, Fe, Mn, Mo, Zn, Co and Ni. If the sources of carbon or nitrogen, or the water used, do not contain these salts or trace elements to a sufficient degree, it is advantageous to supplement the nutrient medium appropriately. The composition of the nutrient media can be varied within wide ranges. The nature and composition of the nutrient media will in general depend on which constituents are particularly advantageously available in each individual case.

In carrying out the process, it can be advantageous to use only relatively low concentrations of the soluble constituents of the nutrient solution at the start of the culture and then to supply these constituents in fractions, in the form of a sterile, relatively concentrated solution, to the culture batch by frequent additions in the course of the first 3 culture stages. The pH value of the growing cultures should preferably be kept from about 6 to 8, especially about 6.5 to 7.5. Too great a drop in pH in the acid range can be avoided by adding an organic or inorganic base, preferably $CaCO_3$. As is customary in fermentation technology, it is also possible to use automatic pH regulation, in which sterile organic or inorganic acid, for example $H_2SO_4$, or sterile alkali, for example NaOH, is injected at intervals into the culture solution.

It is advantageous to ensure that the micro-organisms are adequately brought into contact with oxygen and with the nutrient materials. This can be achieved in accordance with the generally customary methods, such as shaking and stirring.

The culture temperature, in general, can be about 20° to 40° C., preferably about 24° to 35° C.; a temperature of about 28° C. is particularly preferred. The duration of the culture can be varied greatly, with, for example, the composition of the nutrient medium, and the culture temperature, playing a role. The particular optimum conditions can easily be established by anyone skilled in the microbiological field.

It has been found that the amount of the compound according to the invention accumulating in the culture broth in general reaches its maximum about 2 to 12, especially about 5 to 8, days after the start of the culture.

As is general in microbiological processes, extraneous infections of the culture media should be avoided. For this purpose, the usual precautions are taken, such as sterilization of the nutrient media, of the culture vessels and of the air required for aeration. For example, steam sterilization and dry sterilization may be used to sterilize the equipment.

If an undesired amount of foam is produced during the culture, it is possible to add customary chemical anti-foam agents, for example fluid fats and oils, oil-water emulsions, paraffins, higher alcohols, such as octadecanol, silicone oils, polyoxyethylene compounds and polyoxypropylene compounds. Foam can also be suppressed or eliminated with the aid of the conventional mechanical devices (which, for example, use centrifugal forces).

The compound according to the invention can be isolated from the culture medium in accordance with generally customary physico-chemical methods. Isolation can be effected, for example, in accordance with the customary extraction processes and/or precipitation processes and/or chromatography processes. The isolated compound can also be subjected to a fine purification with the aid of the methods mentioned. However, for many cases fine purification is not necessary, since the impurities which may be present do not adversely affect the activity of the compound as a herbicide. In all isolation and purification operations it is necessary to ensure that pH values above about 3.0 are maintained. Inorganic and organic bases may be used to raise the pH value, for example ammonia, alkali metal and alkaline earth metal hydroxides and alkali metal and alkaline earth metal carbonates and bicarbonates, for example KOH, NaOH, $Na_2CO_3$, $NaHCO_3$ and $CaCO_3$, trialkylamines, such as triethylamine, morpholine and pyridine. In order to discover, in the above-mentioned methods of isolation and purification, those fractions in which the compound according to the invention is present in its highest concentration or purity, the customary physico-chemical methods may be employed, for example measuring the UV bands at 259 nm, measuring the $R_f$ values or, preferably, investigating the herbicidal activity.

By way of example, where a liquid aqueous nutrient medium is used, the isolation and purification of the compound according to the invention may be carried out as follows:

After its accumulation in the supernatant culture liquor, the culture filtrate and mycelium are separated by customary methods (for example centrifuging).

The compound according to the invention can be isolated from the culture filtrate and, if desired, purified, with the aid of customary extraction processes and/or precipitation processes and/or chromatographic processes. The chromatography can be carried out in the form of column chromatography. The adsorbents employed can be the customary inorganic or organic adsorbents, for example aluminum oxide, silica gel, manganesium silicate, active charcoal, cellulose, cellulose derivatives, synthetic resins, such as polyamides, polyamide derivatives, for example acetylated polyamide, or dextran gels. A great diversity of solvents or solvent mixtures in which the compound according to the invention is soluble can be used as eluants. The use of water, or of a mixture of water and methanol, or of water and ethanol (for example 1:1 parts by volume) is preferred.

Preferably, chromatographic processes, for example non-specific adsorption or hydrophobic sorbents or ion exchange chromatography, are used to isolate the compound according to the invention. These methods are known from the purification of water-soluble, basic, naturally occurring materials.

For the commercial preparation of the compound according to the invention, it is preferred to isolate it by adsorption and subsequent desorption on a hydrophobic carrier resin (for example Lewapol, a hydrophobic carrier resin from Bayer AG). The desorption can be carried out with, for example, short-chain aliphatic alcohols, preferably methanol or ethanol. The desorption agent should be miscible with water, since the solubility of the compound in anhydrous alcohols is low.

Furthermore, ion exchange chromatography can be carried out, preferably on ion exchangers of the phosphoric acid type (for example phosphocellulose) or of the sulphonic acid type (for example Dowex® 50 grades; sulphonic acid resins from Dow Chem. Corp., Midland, Mich.), although more weakly acid exchangers of the carboxylic acid type (such as, for example, Lewatit® CNP/LF, a weakly acid exchanger from Bayer AG, or Amberlite IRC-50, a weakly acid exchanger from Messrs. Röhm and Haas) can also be employed. The ion exchange can be effected with the aid of gradient elution, for which both pure pH gradients, pure salt gradients and mixed pH/salt gradients can be employed successfully. The ion exchange can also be effected by the "batch" process, wherein preferably higher salt concentrations in water (for example 1 M ammonium formate in water) are used for the desorption; desorption can also be achieved by increasing the pH value (for example to pH 10).

A fraction prepurified in this way can again be purified by the customary methods. Preferably, gel diffusion chromatography can be employed for this purpose. Chromatography on highly crosslinked polyacrylamide gels (for example on Biogel® P-2) proves successful, but the compound according to the invention can also be isolated with the aid of dextrans (for example Sephadex® G-10). Preferably, this takes place in the presence of monovalent ions, in order to avoid non-specific interactions between the carrier materials and the compound to be developed chromatographically. A product obtained in this way is in general more than 80% pure.

The pure compound according to the invention can be isolated from such a fraction by means of the customary biochemical methods. Amongst the adsorbents already mentioned, cellulose can be employed particularly successfully. An example of an eluant which is used successfully is chloroform-methanol (about 4/1 parts by volume).

The compound can be obtained from its solutions in accordance with the customary methods, for example evaporation of the solvent or freeze-drying.

The new strains of Streptosporangium, carrying the laboratory designations SS 237, SS 243, SS 248 and SS 268, were deposited under the following numbers at the Centraalbureau voor Schimmelculturen, Baarn, Netherlands:

| | |
|---|---|
| SS 237 | CBS 545.77 |
| SS 243 | CBS 544.77 |
| SS 248 | CBS 543.77 |
| SS 268 | CBS 542.77 |

The invention also relates to new micro-organisms of the family of the Actinoplanaceae, which, when cultured in a nutrient medium containing sources of carbon and sources of nitrogen as well as mineral salts, produce a compound of the empirical formula $C_{10}H_{14}N_6O_3$, which essentially shows the IR KBr-absorption spectrum reproduced in FIG. 2.

Amongst these, new micro-organisms of the genera Actinoplanes, Ampulariella, Pilimelia and especially Streptosporangium are particularly important within the scope of the present invention.

The active compound according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired. Whether the compound according to the invention acts as total herbicides or selective herbicides depends essentially on the amount used.

The active compound according to the present invention may be used, for example, to combat the following plants: dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

The active compound according to the present invention may be used, for example, as a selective herbicide in the following cultures:

Dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compound according to the invention is in no way restricted to these genera but also embraces other plants, in the same way.

Depending on the concentrations, the compound can be used for the total combating of weeds, for example on industrial terrain and railway tracks and on paths and squares with or without trees. Equally, the compound can be employed for combating weeds in perennial cultures, for example afforestations, decorative tree plantings, orchards, vineyards, citrus groves, nut orchards, banana plantations, coffee plantations, tea plantations, rubber plantatations, oil palm plantations, cacao plantations, soft fruit plantings and hopfields, and for the selective combating of weeds in annual cultures.

The active compound can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compound with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound according to the invention, either as such or in its formulations, can also be used, for the combating of weeds, in admixture with known herbicides, finished formulations or tank mixing being possible.

The active compound according to the invention can be present in the formulations as a mixture with other active compounds, such as fungicides, insecticides, acaricides, nematicides, herbicides, bird repellents, growth factors, plant nutrients and agents for improving soil structure.

The active compound can be used as such, as its formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

The compound according to the invention can be applied after or, in particular, before emergence of the plants.

The amount of active compound used can vary within relatively wide limits. It depends essentially on the nature of the desired effect. In general, the amounts used are between 0.1 and 40 kg of active compound per ha, preferably between 0.1 and 10 kg/ha.

The present invention also provides a herbicidal composition containing as active ingredient the compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof the compound of the present invention alone or in the form of a composition containing as active ingredient the compound of the present invention in admixture with a diluent or carrier.

The present invention further provides crops protected from damage by weeds by being grown in areas in which immediately prior to and/or during the time of the growing the compound of the present invention was applied alone or in admixture with a diluent or carrier.

It will be seen that the usual methods of providing a harvested crop may be improved by the present invention.

In the accompanying drawings.

Figure 1:
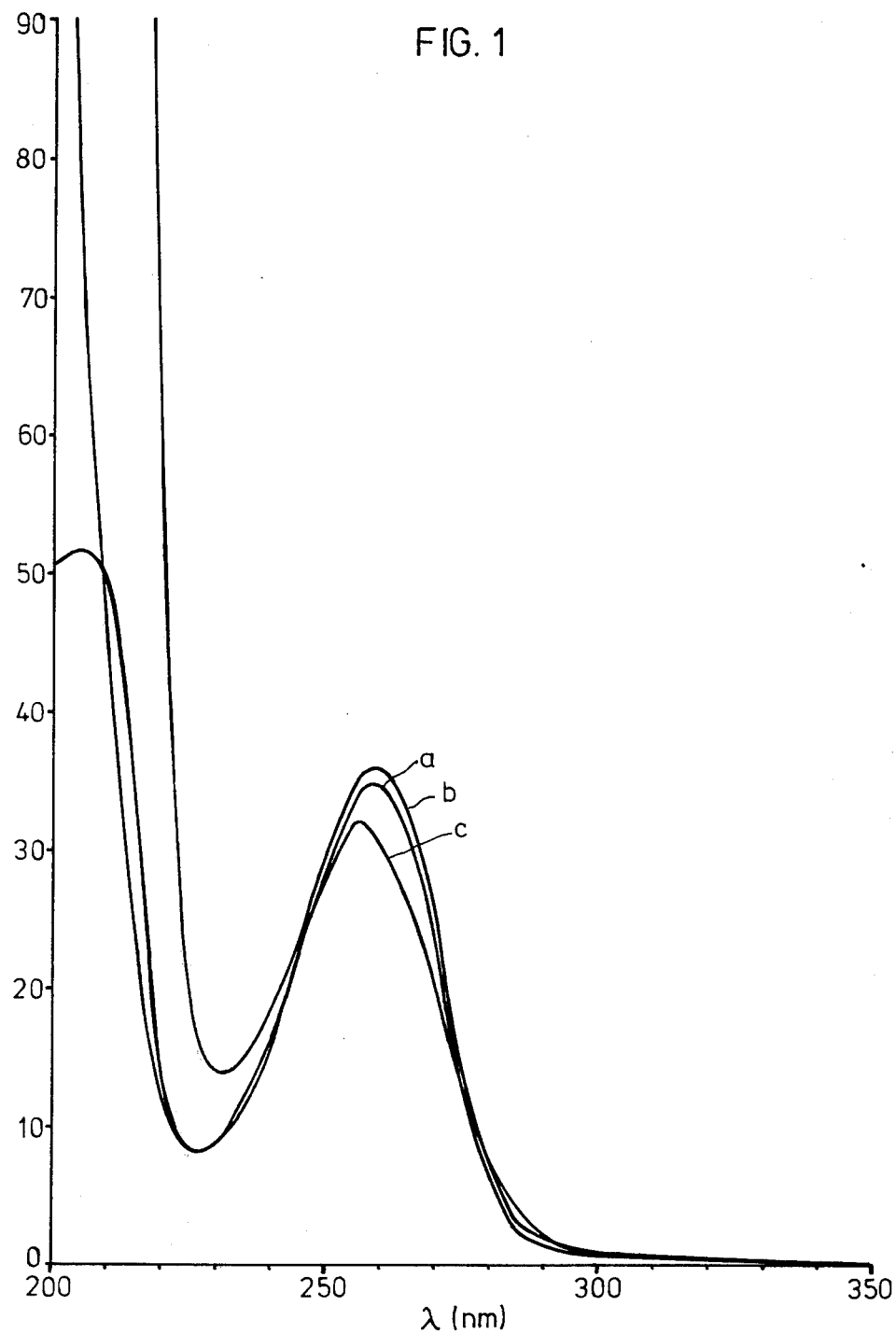
FIG. 1 is a UV spectrum of the novel compound produced by the process of Example 15.
Figure 2:
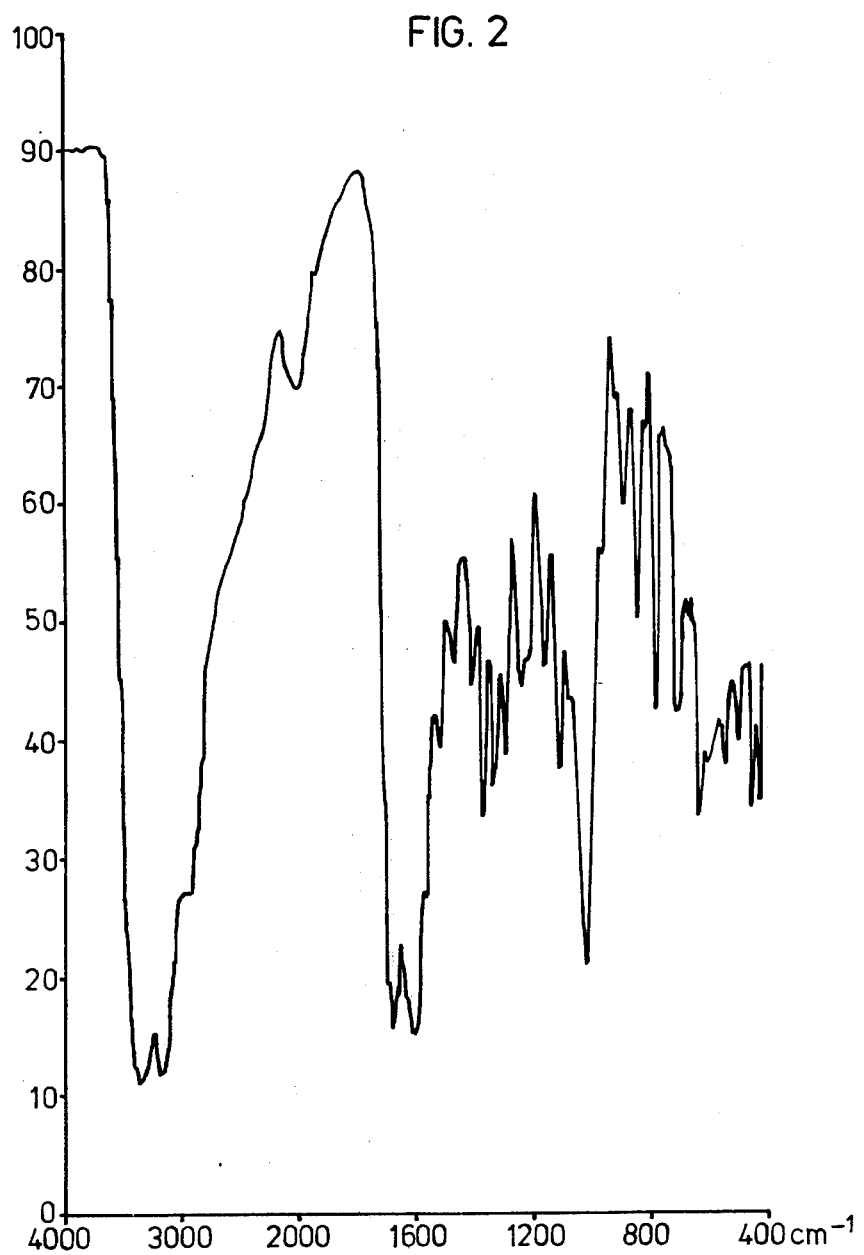
FIG. 2 is an IR absorption spectrum of the novel compound.
Figure 3:
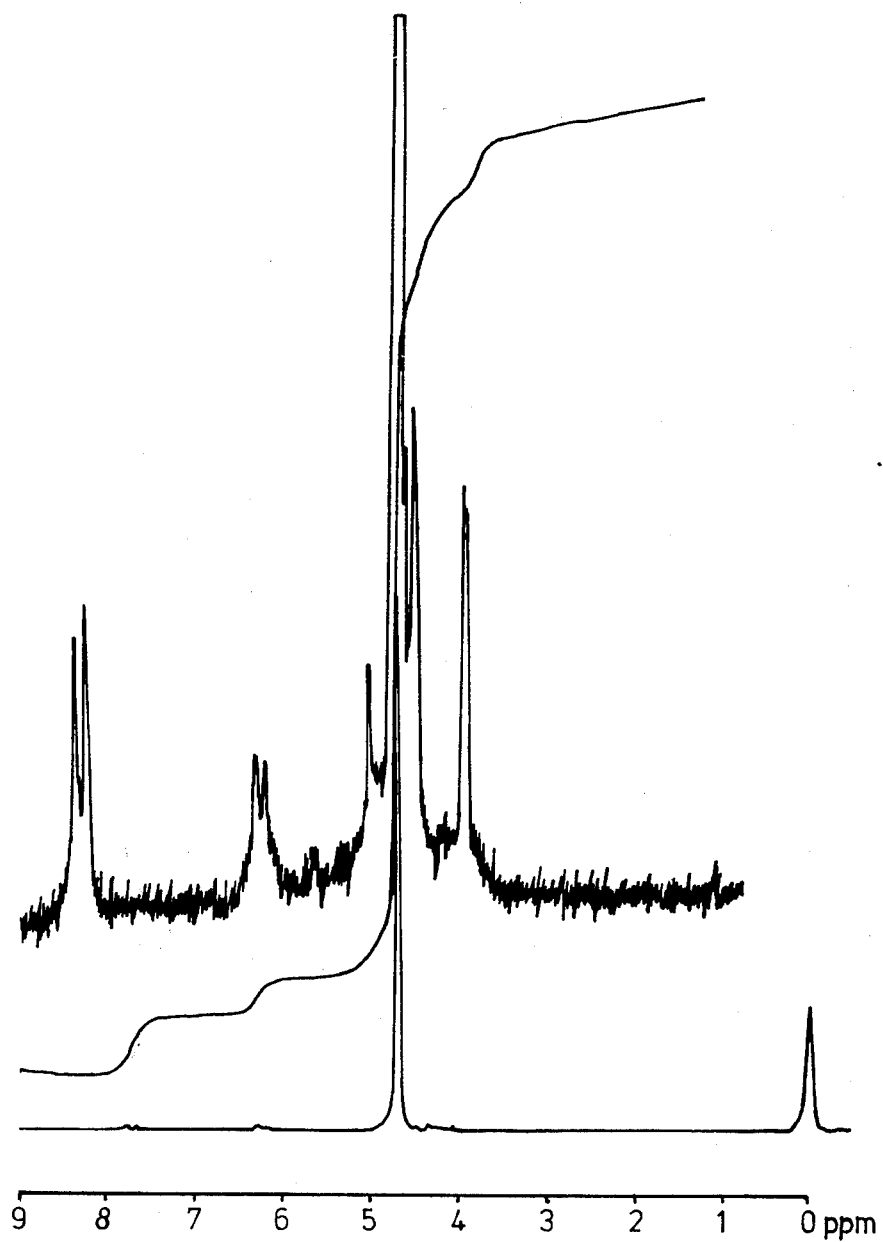
FIG. 3 is a $^1$H 60 Mc/s nuclear resonance spectrum of the novel compound.
Figure 4:
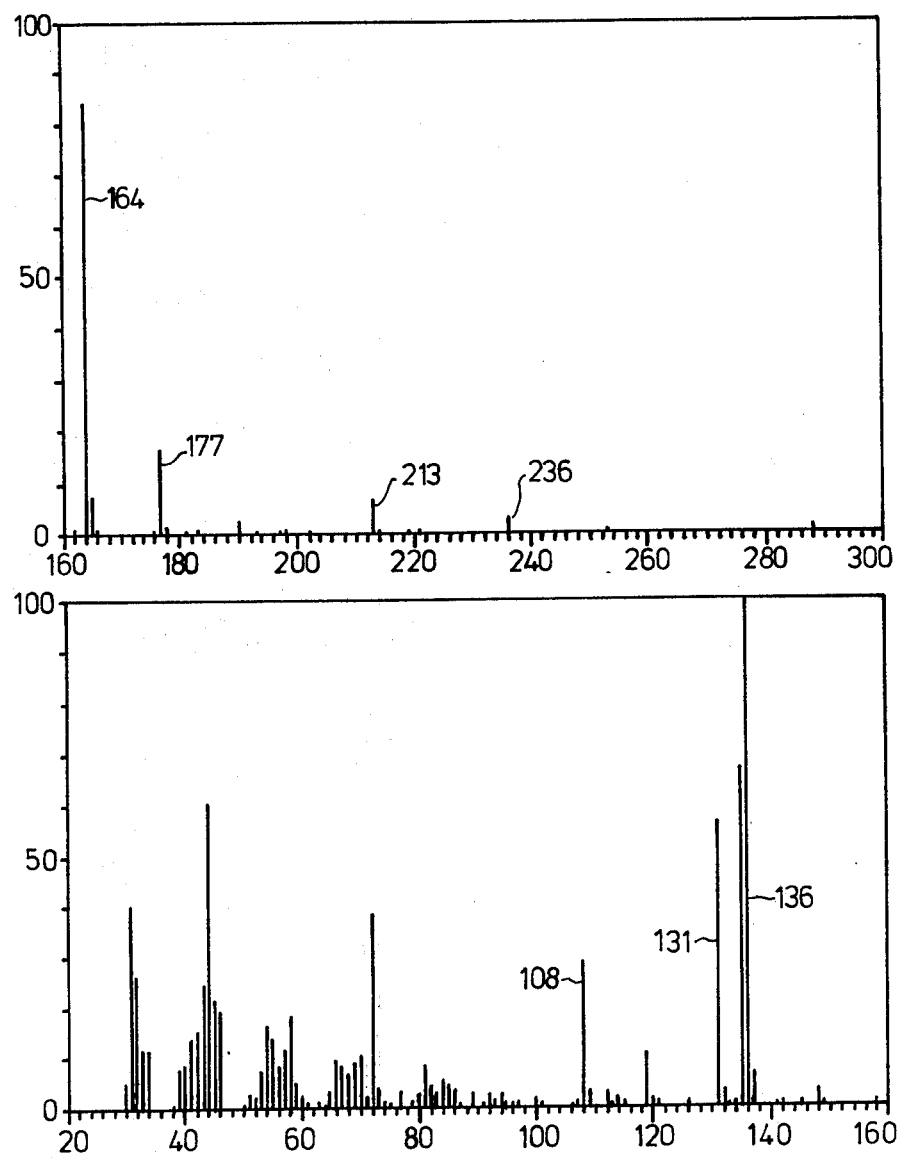
FIG. 4 is a mass spectrum of the novel compound.

The preparation of the novel compound is illustrated in the following examples:

EXAMPLE 1

1-liter Erlenmeyer flasks which contained 120 ml of a nutrient solution comprising 0.5% of $(NH_4)_2SO_4$, 0.3% of $KNO_3$, 0.4% of soy flour, 0.4% of corn steep liquor, 6.0% of starch and 0.5% of $CaCO_3$ (pH adjusted, before sterilization, to 7.0 with KOH, sterilization for 30 minutes at 121° C.) were each inoculated with 4 ml of a pre-culture (obtained in the same nutrient solution, inoculated with a slant tube culture) of the strain SS 237, and this culture was incubated at 28° C. on a rotary shaking machine. A culture broth was obtained after a period of culture of 5 days, in which the content of active compound was found to be 2.8 mg/liter when determined in accordance with Example 17.

EXAMPLE 2

A fermenter containing 100 liter of a nutrient solution according to Example 1 was inoculated with 3 liters of a pre-culture, obtained in a shaking flask, of the strain SS 237, and incubation was carried out with stirring and aeration for 6 days at 28° C. A culture broth was obtained, from which, after adsorption on a hydrophobic carrier resin based on a sulphonic acid, for example Lewapol (column 30×50 cm, flow rate 20 liters/hour) and desorption by means of 50 liters of 50% strength methanol (flow rate 20 liters/hour), a preparation was obtained, in the lyophilizate of the desorbate, which, in a herbicide test on cress, using an amount of 1.5 kg/ha and employing the pre-emergence test according to Example A, gave 80% destruction.

EXAMPLE 3

A 1-liter Erlenmeyer flask which contained 120 ml of a nutrient solution comprising 2% of starch, 1% of glucose, 0.5% of casein hydrolysate and 1.0% of yeast extract, the nutrient solution having been brought to pH 7.2 with $Na_2CO_3$, then treated with 0.4% of $CaCO_3$, and sterilized for 30 minutes at 121° C., was inoculated with 80 ml of a pre-culture of the strain SS 243, obtained from the same nutrient solution, and was incubated on a rotary shaking machine. A culture broth was obtained, after 6 days, in which the content of active compound was found to be 2.8 mg/liter when determined in accordance with Example 17.

EXAMPLE 4

A batch according to Example 3 was inoculated with a pre-culture of the strain SS 248. A culture broth was obtained, after 6 days' incubation at 28° C., in which the content of active compound was found to be 4.7 mg/liter when determined in accordance with Example 17.

EXAMPLE 5

A 1 liter Erlenmeyer flask which contained 120 ml of a nutrient solution, comprising 1% of glucose, 1% of starch, 0.5% of casein hydrolyzate, 0.75% of meat extract, 0.75% of peptone, 0.5% of yeast extract, 0.1% of $K_2HPO_4$, 0.3% of NaCl and 0.1% of $MgSO_4$, the pH being brought to 7.2 before sterilization and the nutrient solution being sterilized for 30 minutes at 121° C., was inoculated with 8 ml of a pre-culture of the strain SS 268, obtained in the same culture solution, and was incubated on a rotary shaking machine for 6 days at 28° C. A culture broth was obtained, in which the content of active compound was found to be 23.8 mg/liter when determined in accordance with Example 17.

EXAMPLE 6

The procedure according to Example 5 was followed, but with a nutrient solution without glucose. A culture broth was obtained, after 3 days' incubation, in which the content of active compound was found to be 24.6 mg/liter when determined in accordance with Example 17.

EXAMPLE 7

The procedure of Example 6 was followed, but at 24° C. A determination of the content, in accordance with Example 17, after 4 days' incubation gave a value of 24.1 mg of active compound per liter.

EXAMPLE 8

In Example 5, the glucose was replaced by starch. A determination of the content, in accordance with Example 17, after 4 days gave a value of 29.5 mg of active compound per liter.

EXAMPLE 9

In Example 5, the glucose was replaced by sucrose. A determination of the content, in accordance with Example 17, after 4 days gave a value of 30.8 mg of active compound per liter.

EXAMPLE 10

In Example 5, the glucose was replaced by galactose. A determination of the content, in accordance with Example 17, after 5 days gave a value of 38.3 mg of active compound per liter.

EXAMPLE 11

The procedure of Example 5 was followed, but without casein hydrolyzate. A determination of the content, in accordance with Example 17, after 5 days' incubation, gave a value of 13.4 mg of active compound per liter.

EXAMPLE 12

The procedure of Example 5 was followed, but with 1% of casein hydrolyzate. A determination of the content, in accordance with Example 17, after 5 days' incubation, gave a value of 10.5 mg of active compound per liter.

EXAMPLE 13

The procedure of Example 5 was followed, but without meat extract. A determination of the content, in accordance with Example 17, after 5 days' incubation, gave a value of 13.1 mg of active compound per liter.

EXAMPLE 14

The procedure of Example 5 was followed, but with 1.5% meat extract. A determination of the content, in accordance with Example 17, after 5 days' incubation, gave a value of 14.5 mg of active compound per liter.

EXAMPLE 15

In a fermentation according to Example 2, 85 liters of supernatant culture liquor were obtained after centrifuging off the mycelium.

The supernatant culture liquor was applied, at the rate of 20 liters/hour, to a column (30×50 cm) which contained a hydrophobic carrier resin based on a sulphonic acid (for example Lewapol), and the column was rinsed with 50 liters of $H_2O$. The material passing through the column, and the wash water, were inactive and were discarded. Desorption was then carried out with 50 liters of 50% strength methanol and the desorbate was concentrated to about 2 liters in a rotary evaporator, and lyophilized (yield: 1,039 g). To complete the desorption, the column packing was rinsed with 50 liters of 100% strength methanol, the eluate was concentrated to dryness, the residue thus obtained was taken up in 2 liters of water and the suspension was lyophilized (yield: 20.4 g). The desorbate of the carrier resin obtained with 50% strength methanol exhibited the herbicidal action.

1 kg of phosphocellulose (H+ form) was added to a solution of 150 g of the 50% desorbate from the Lewapol, in 20 liters of 0.01 M ammonium formate buffer of pH 3.6. The mixture was stirred for 1 hour and then filtered on a suction filter (filter K3); the filtrate was concentrated and lyophilized (yield 89.1 g). The lyophilizate was inactive in a herbicide test. The phosphocellulose was introduced into 10 liters of 1 M ammonium formate solution and the mixture was stirred for 1 hour and again suction-filtered. The lyophilizate of the filtrate (1.53 g) contained the herbicidally active component.

1.5 g of ammonium formate desorbate of the phosphocellulose were treated with 20 ml of $10^{-2}$ M ammonium formate solution, the soluble constituent was centrifuged off (the residue was inactive) and the supernatant liquor was applied to a Biogel P-2 column (5×100 cm, equilibrated with $10^{-2}$ M ammonium formate solution). The eluate was separated into 6 fractions; fraction D showed the herbicidal action (yield: 74 mg).

The purity of the fraction obtained from the separation on Biogel P-2 (polyacrylamide gel from Messrs. Bio-Rad) was tested by thin layer chromatography. It was found that the fraction was not yet chemically a single compound. Hence, a solution of 70 mg of fraction D in 2 ml of chloroform/methanol=4/1 was fractionated by preparative paper chromatography (paper: Whatman 3 mm, migrating agent chloroform/methanol=4/1). Four zones were eluted with water. The second zone ($R_f$=0.05–0.12) contained the herbicidal active compound (26 mg).

EXAMPLE 16

85 liters of a culture filtrate according to Example 2 were adsorbed on a hydrophobic carrier resin based on a sulphonic acid, for example Lewapol (column 30×50 cm, flow rate 20 liters/hour), and desorption was then carried out with 50 liters of 50% strength methanol; subsequent lyophilization gave 147 g of a crude preparation. 5 g of this crude preparation could be subjected to preparative high pressure liquid chromatography on silica gel (pre-packed column for preparative HPLC, system LC 50, Messrs. Waters) in chloroform/methanol in a volume ratio of 1/1. For this purpose, a solution of 5 g of 50% strength methanolic desorbate from the Lewapol was dissolved in 50 ml of migrating agent and injected for development. The flow rate was 250 ml/hour. Under these conditions, the retention time of the active compound was 7 minutes 20 seconds. After the lyophilization, 379 mg of white amorphous powder were obtained; this material was herbicidally active when used in accordance with Example 20, in an amount of 1.25 kg/ha.

EXAMPLE 17

100 μl of 1 M acetate buffer of pH 3.5 were added to 10 ml of a culture filtrate according to Example 3. The mixture was stirred for 30 minutes and then centrifuged. 500 mg of phosphocellulose (H+ form) were added to the supernatant liquor. The suspension was stirred for 10 minutes and then centrifuged. In this procedure, the herbicide became bound to the ion exchanger. 5 ml of 1 N ammonium formate solution were added to the sediment (phosphocellulose) and the mixture was again stirred for 10 minutes and then centrifuged. The supernatant liquor was concentrated to dryness on a rotary evaporator. In order to keep low the salt content of the solution subsequently used for thin layer chromatography, the residue was taken up in 1 ml of 90% strength methanol. The mixture was again centrifuged and 10 μl of the supernatant liquor were employed for thin layer chromatography (solution I). The chromatography was carried out on silanized silica gel plates with a fluorescence indicator. Development was carried out in chloroform/methanol/0.01 M tris/HCl buffer of pH 3.0 (volume ratio 4/1/0.02) as the migrating agent, over a distance of 15 cm. The profile of the fluorescence extinction was recorded on a thin layer chromatography scanner (T-scanner of Messrs. Carmag) (conditions: 1 point diaphragm, primary filter 810, secondary filter 2A+10% 823, slit width 5 mm). The herbicide had an $R_f$ value of 0.26.

10 μl portions of solution I were chromatographed, with the herbicide according to Example 15 as the comparison substance, on Kieselgel 60, F 254 (Messrs. Merck). The following were used as migrating agents:

(1) n-butanol/glacial acetic acid/$H_2O$=50/25/25
(2) iso-propanol/2 N ammonia/$H_2O$=70/10/20
(3) n-butyl acetate/n-butanol/glacial acetic acid/-phosphate buffer of pH 7=50/10/25/15.

The active compounds according to Examples 1 and 3 exhibited identical behavior in thin layer chromatography (migrating agent 1): $R_f$=0.27; (migrating agent 2): $R_f$=0.40 and (migrating agent 3): $R_f$=0.08).

Both active compounds could be stained with 4-dimethylaminobenzaldehyde, ninhydrin and Morgan-Elson's reagent.

The quantitative determination of the herbicide in the culture filtrate according to Examples 1 to 14 was carried out after working up, by scanning the developed thin layer chromatogram. The recorded peaks were cut out and the weight of the paper was determined. For the pure substance, a paper weight of about 28 mg was found for 50 μg.

EXAMPLE 18

5 ml of fraction D according to Example 15 were employed in preparative thin layer chromatography on silica gel (Kieselgel 60, 2.5 mm, Messrs. Merck). Chloroform/methanol in the volume ratio of 80/20 was used as the migrating agent. Development was carried out over 15 cm. The zone at 1.5 cm–2.5 cm distance from the start was scraped out, eluted with 5 ml of water and the eluate lyophilized. 12.5 mg of pure active compound were obtained.

EXAMPLE 19

5 ml of fraction D according to Example 15 were employed in preparative paper chromatography (3 mm paper, Messrs. Whatman). Chloroform/methanol=4/1 was used as the migrating agent. Development took place over 30 cm. The zone at 1.5 cm–3.6 cm distance from the start line was cut out and the paper was twice eluted with 10 ml of water at a time. After lyophilization, 14.1 mg of pure active compound were obtained.

The herbicidal activity of the compound of this invention is illustrated by the following examples:

EXAMPLE 20

Pre-emergence test

Cress (*Lepidium sativum*) seeds were set out in dishes filled with vermiculite. The dishes were then watered with a Hoagland nutrient solution to which the active compound according to the invention had been added.

After 2 weeks, the degree of damage of the plants was assessed in % damage in comparison to the development of the untreated control.

The preparations according to the above preparative examples exhibited a high activity.

EXAMPLE 21

Post-emergence test

Cress (*Lepidium sativum*) seeds were set out in dishes filled with vermiculite. The dishes were then watered with a Hoagland nutrient solution, until the plants had reached a size of 5–10 cm.

The plants were then sprayed with a preparation of active compound.

After 2 weeks, the degree of damage of the plants was assessed in comparison to the development of the untreated control.

The preparations according to the above preparative examples exhibited a high activity.

It will be appreciated that the instant specification and examples are set forth by way of illustration and not limitation, and that various modifications and changes may be made without departing from the spirit and scope of the present invention.

What is claimed:

1. A compound of the empirical formula $C_{10}H_{14}N_6O_3$, having an IR KBr-absorption spectrum exhibiting characteristic bands at wave numbers 3340, 3170, 2920, 2040, 1660, 1600, 1570, 1520, 1480, 1430, 1380, 1340, 1295, 1250, 1215, 1160, 1110, 1030, 890, 860, 790 and 720 cm$^{-1}$, and a specific optical rotation at 1% in methanol at 20° C. of $-19.7°$.

2. The compound of claim 1 in pure form.

3. A herbicidal composition comprising at least about 0.1% by weight of the compound of claim 1 and a diluent.

4. A composition according to claim 3, wherein the compound is present in at least about 0.5% by weight on a dry basis.

5. A method of combating weeds which comprises applying to the weeds, or to a habitat thereof, a herbicidally effective amount of the compound according to claim 1.

6. The method according to claim 5, in which the active compound is applied to an area of agriculture in an amount of about 0.1 to 40 kg per hectare.